United States Patent
Rattner et al.

(10) Patent No.: US 9,119,745 B2
(45) Date of Patent: Sep. 1, 2015

(54) ADHERENT COVER AND DISPENSER

(76) Inventors: Ehud Rattner, Haifa (IL); Nimrod Rotem, Haifa (IL)

(*) Notice: Subject to any disclaimer, the term of this patent is extended or adjusted under 35 U.S.C. 154(b) by 396 days.

(21) Appl. No.: 13/265,949

(22) PCT Filed: Apr. 22, 2010

(86) PCT No.: PCT/IL2010/000324
§ 371 (c)(1),
(2), (4) Date: Oct. 24, 2011

(87) PCT Pub. No.: WO2010/122559
PCT Pub. Date: Oct. 28, 2010

(65) Prior Publication Data
US 2012/0037656 A1   Feb. 16, 2012

Related U.S. Application Data

(60) Provisional application No. 61/171,855, filed on Apr. 23, 2009.

(51) Int. Cl.
| | |
|---|---|
| B65D 83/00 | (2006.01) |
| B32B 33/00 | (2006.01) |
| C09J 7/02 | (2006.01) |
| B65G 59/00 | (2006.01) |
| A61F 13/02 | (2006.01) |
| A61F 15/00 | (2006.01) |

(52) U.S. Cl.
CPC ............. *A61F 13/02* (2013.01); *A61F 13/0269* (2013.01); *A61F 15/002* (2013.01); *Y10T 428/1471* (2015.01)

(58) Field of Classification Search
USPC ........... 221/25, 33–36, 47, 52, 56, 59, 63, 92, 221/303, 306
See application file for complete search history.

(56) References Cited

U.S. PATENT DOCUMENTS

| | | | | |
|---|---|---|---|---|
| 1,072,859 | A | * | 9/1913 | Kingsley .......................... 221/59 |
| 4,418,822 | A | * | 12/1983 | Dotta ............................ 206/441 |
| 4,832,008 | A | * | 5/1989 | Gilman .......................... 602/57 |
| 4,913,138 | A | * | 4/1990 | Yoshida et al. ................. 602/57 |
| 5,271,522 | A | | 12/1993 | Ko et al. |
| 6,446,795 | B1 | * | 9/2002 | Allen et al. .................... 206/210 |
| 6,923,320 | B2 | | 8/2005 | Grossman |
| 8,240,472 | B2 | * | 8/2012 | Khan ............................ 206/440 |
| 8,794,293 | B2 | * | 8/2014 | Rice et al. ..................... 156/578 |
| 2007/0293830 | A1 | | 12/2007 | Martin |
| 2008/0308571 | A1 | | 12/2008 | Rattner |
| 2010/0222731 | A1 | * | 9/2010 | Gajiwala ........................ 602/57 |

* cited by examiner

*Primary Examiner* — Gene Crawford
*Assistant Examiner* — Kelvin L Randall, Jr.
(74) *Attorney, Agent, or Firm* — Browdy and Neimark, PLLC

(57) ABSTRACT

A dispenser for sticky articles and a sticky article, A sticky article comprising: a skin-adherent cover, a first and a second handle and a first and a second protective element, the cover comprising: a side comprising skin-adhesive material, an opposite side and edges; the protective elements protective of the cover, each protective element extending to or beyond all edges of the cover, the first said protective element adhering to the cover opposite side and the second said protective element coupled to the cover side comprising skin-adhesive material, said first handle coupled to the first protective element and said second handle coupled to the second protective element, said first protective element configured to adhere to the cover less than the cover adheres to skin, wherein the article is configured to allow detachment of said second element and second handle from said cover when said first and second handles are pulled apart.

5 Claims, 23 Drawing Sheets

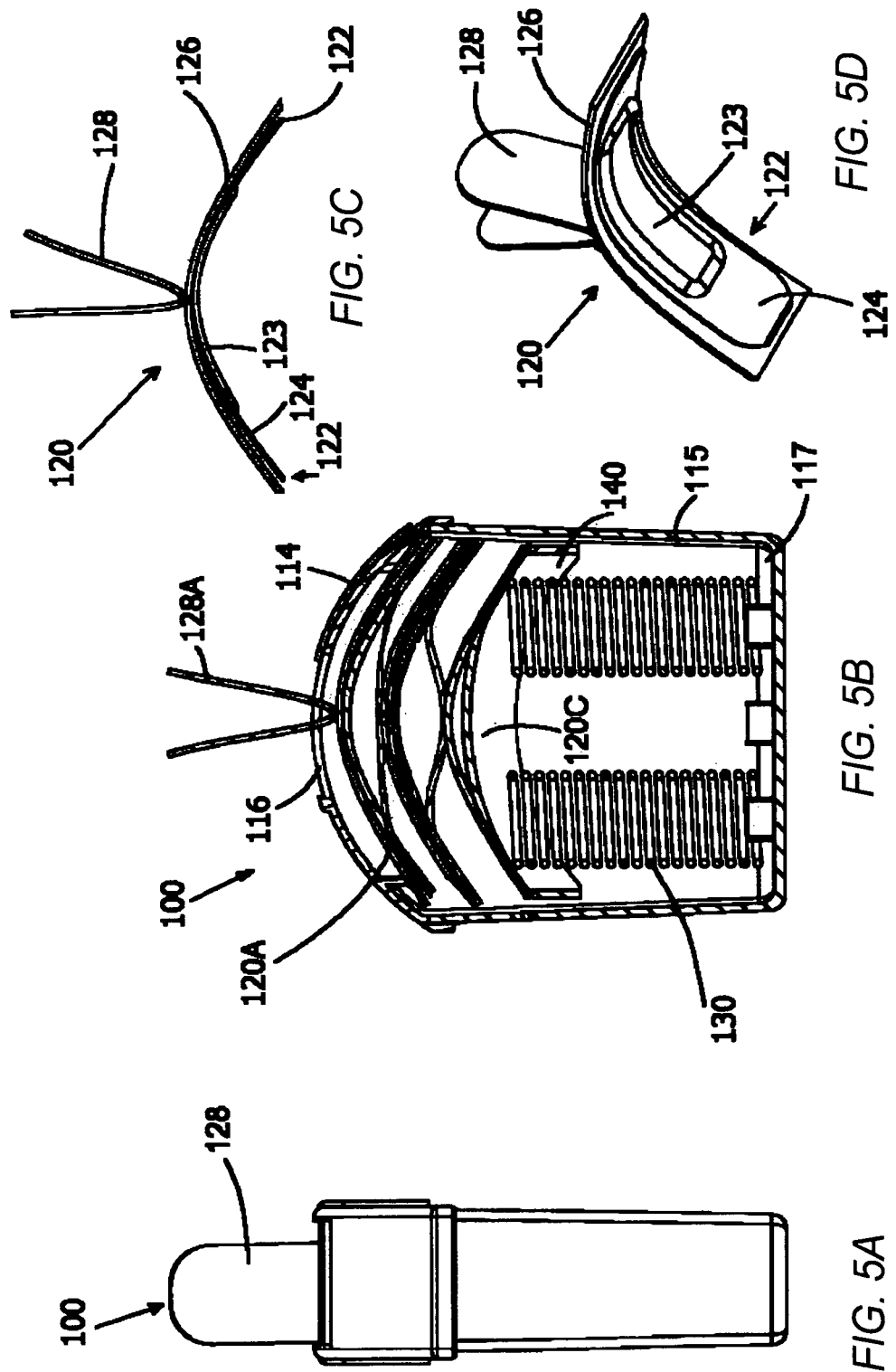

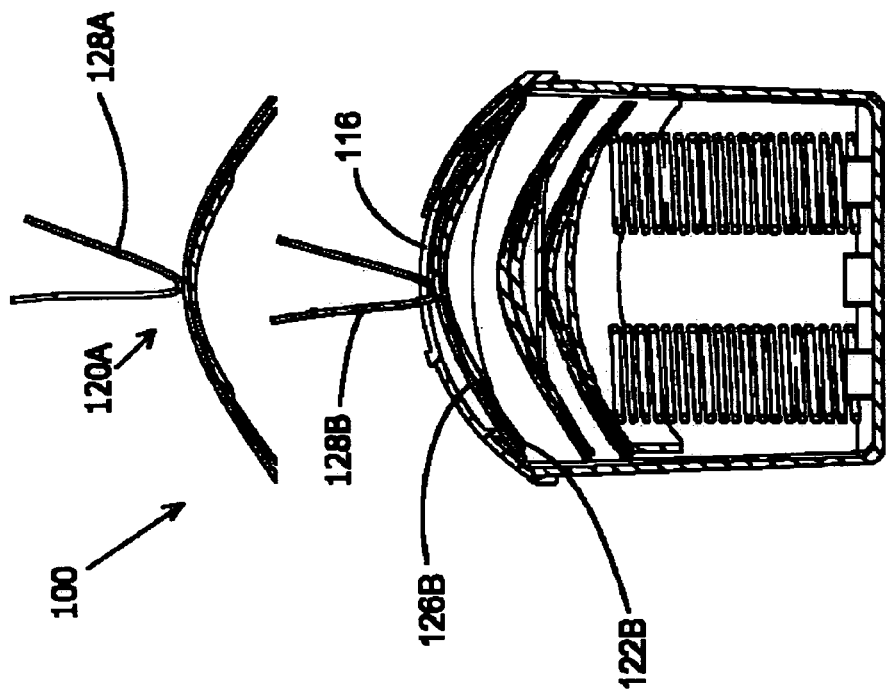
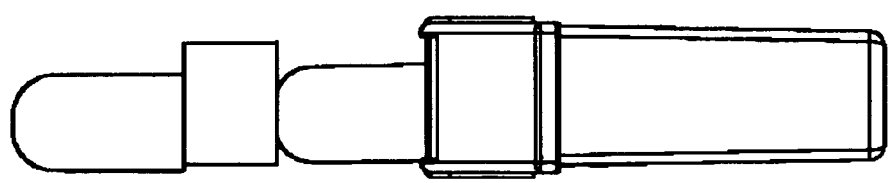

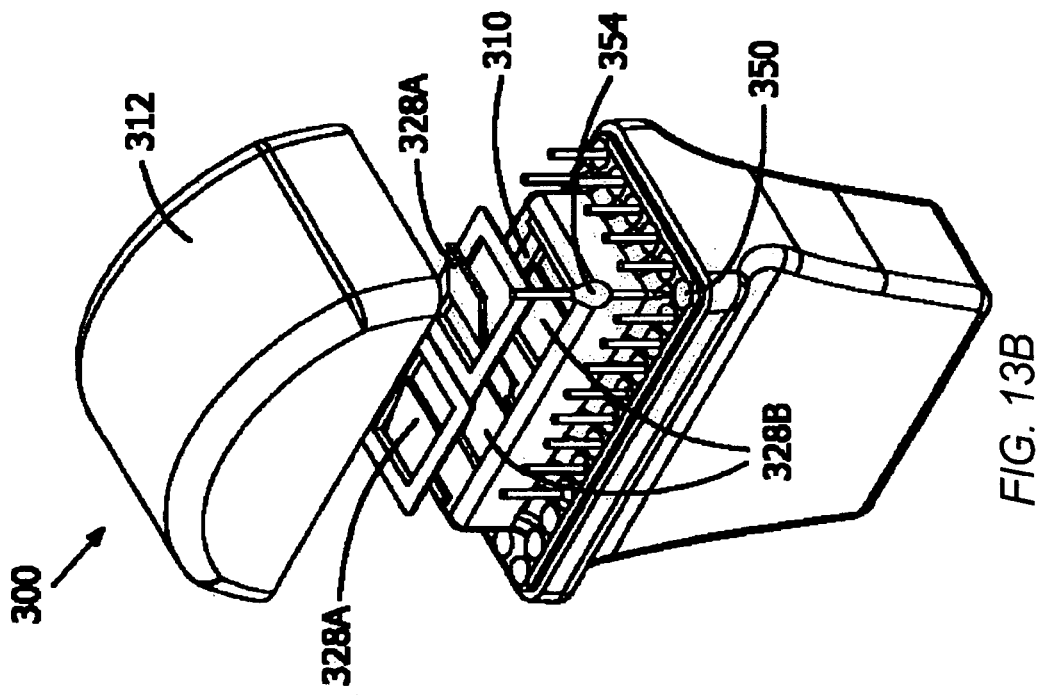
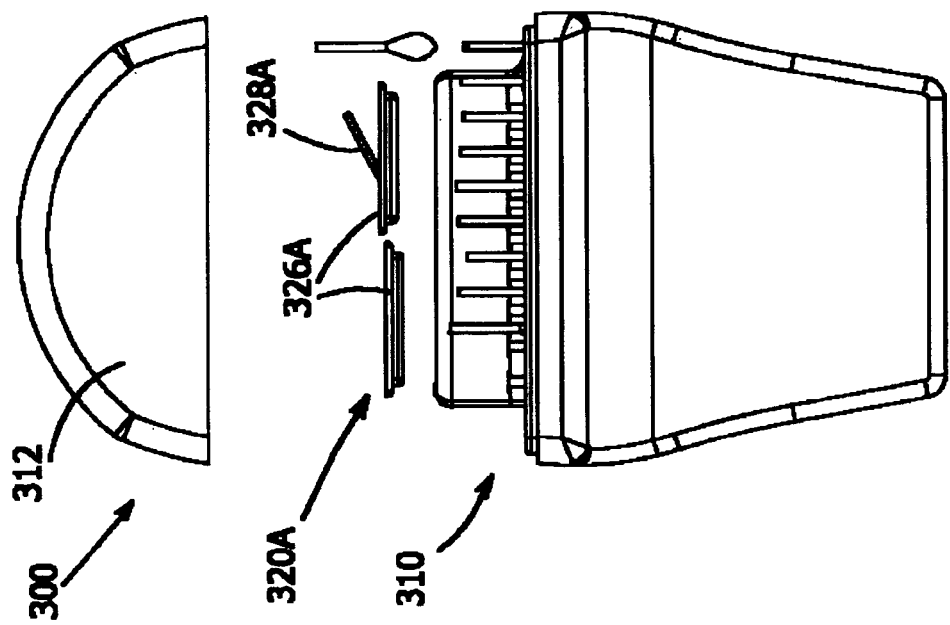
FIG. 13B
FIG. 13A

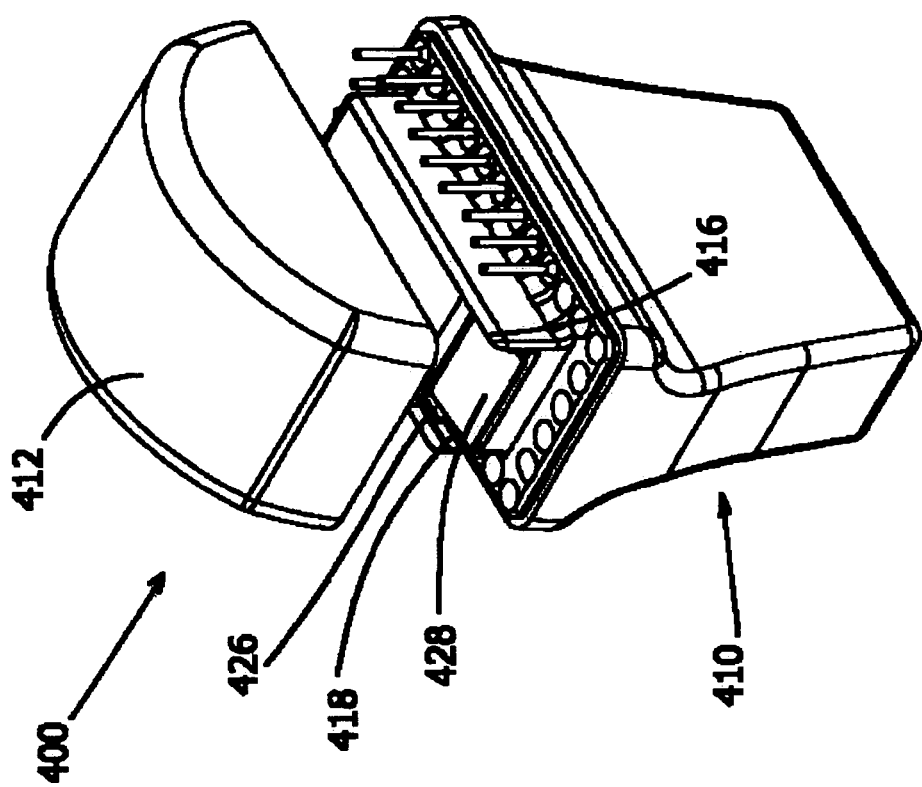
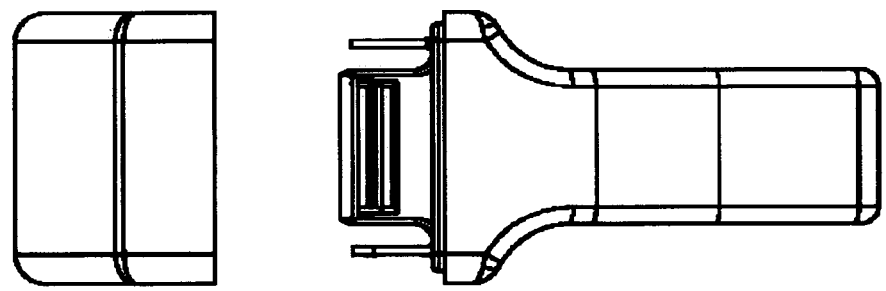
FIG. 16B
FIG. 16A

ADHERENT COVER AND DISPENSER

FIELD OF THE INVENTION

The present invention relates to adherent covers and their dispensers.

BACKGROUND OF THE INVENTION

A bandage are typically used to decrease prolonged loss of body fluids and stop bleeding by covering and protecting wounds such as cuts, scrapes, blisters, bruises and the like. Therefore, bandages are extensively used in hospitals, schools, at home, and basically anywhere.

Most adhesive articles including sticky skin covers such as bandages, plasters and skin patches, are packed in bulks of individual articles; however, some dispensers were developed over the years as an answer to a prolonged need.

An example is disclosed in U.S. Pat. No. 5,358,140 "Adhesive bandage dispensing system" by Pellegrino. The dispensing system includes an elongated strand of individually sterile-wrapped adhesive bandages and a reusable dispenser for dispensing the bandages. Each bandage is contained in a separate sterile compartment of an otherwise continuous wrapping material.

Another individual bandage dispenser is described in U.S. Pat. No. 5,271,522 "Individual bandage dispenser" by Ko et al., wherein the bandages are adhered to successive bandages along away from ends of the bandage. The bandages are dispensed from a gap in a top wall of a box.

The dispensers described above still require high dexterity from their user in order to be properly used, for example in removing the base layers from the adhesive material, and using the correct amount of force to pull the articles out of a gap in the top of the dispenser yet avoid tearing them off before they are fully out of the gap, and therefore merely organize the individual articles and dispense them individually.

Publication WO2008/122982 describes an adhesive bandage dispenser suitable for use by layperson that includes: a cartridge having walls, bottom, and upper opening; a plurality of stacked plates accommodated within the cartridge; a resilient element provided within said cartridge beneath a lowermost plate, wherein said resilient element is adapted to push said plurality of stacked plates toward said upper opening; an adhesive bandage mounted onto each one of said plurality of plates wherein adhesive material of said adhesive bandage is exposed, and an ejection mechanism adapted to eject an uppermost plate of said plurality of plates so as to allow a sequential plate to move upwardly towards said upper opening.

The adhesive dispenser in WO2008/122982, as shown in the figures therein, has adhesive bandages mounted onto each one of said plurality of plates such that the adhesive material (and the sterile pad) of said adhesive bandage is exposed on the side of the plate facing the upper opening. It is envisioned that in certain circumstances the upward exposure of the sterile pad is undesirable, for example small children may accidentally eject an uppermost plate without actually using the bandage mounted on the plate, or apply the bandage a long delay after exposing it to the atmosphere.

Furthermore, although the bandage dispenser described in WO2008/122982 is simple and easy to use and manufacture, further simplification of the dispenser is possible, while retaining all of the advantages of the dispenser described in WO2008/122982.

There is still a need for new dispensers for adhesive articles in any size, of simple construction and simple to operate, that organizes the articles and dispenses them individually without the need to handle the exposure of the adhesive portions, so that the skin-adherent covers in the articles can be immediately and safely adhered onto skin without wasting valuable time.

SUMMARY OF THE INVENTION

One object is to provide embodiments of:

A sticky article comprising: a skin-adherent cover, a first and a second handle and a first and a second protective element, the cover comprising: a side comprising skin-adhesive material, an opposite side and edges;

the protective elements protective of the cover, each protective element extending to or beyond all edges of the cover, the first protective element adhering to the cover opposite side and the second protective element attached to the cover side comprising skin-adhesive material, said first handle coupled to the first protective element and said second handle coupled to the second protective element, said first protective element configured to adhere to the cover less than the cover adheres to skin, wherein the article is configured to allow detachment of said second element and second handle from said cover when said first and second handles are pulled apart.

The articles may further comprise at least one liner non-adherently contacting the skin-adhesive material, and the second protective element adhering to the first protecting element.

In some embodiments the articles are in a stack, wherein the second handle of each article above the bottom article in the stack is the first handle of the adjacent article below.

Some embodiments provide a dispenser comprising at least one stack of articles, the dispenser further comprising a cartridge having walls, bottom and upper opening.

The covers may be selected from one or more of the group: skin patch, poultice, plaster and bandage.

In some embodiments, a sticky article dispenser comprises a cartridge, at least one stack of articles and at least one resilient element, the cartridge having walls, at least one bottom, at least one cartridge opening and at least one cap, each cap configured to snugly cover a cartridge opening;

each article comprising:
a skin-adherent cover, handle and protective element, the cover comprising: a side comprising skin-adhesive material, an opposite side and edges, the edges facing cartridge walls;

the skin-adhesive material being on the side of the cover facing away from a cartridge opening;

the handle coupled to the protective element, the protective element attached to the side of the cover facing said cartridge opening, the protective element extending to or beyond all edges of the cover, said protective elements configured to:
protect the covers from said walls of the cartridge;
adhere to a cover less than the cover adheres to skin;
the at least one resilient element within the cartridge positioned in the cartridge below the stacks and configured to urge the skin-adherent articles in the stacks toward said cartridge opening, the dispenser configured to allow removal of a top article from a stack out of said cartridge opening.

The dispenser may be further configured to seal the skin-adherent covers from the environment outside the cartridge.

The dispenser may be further configured to protect a cover from an adjacent article in the stack.

The resilient elements may comprise at least one spring placed beneath the stacks.

The protective elements may be resilient cards;

the handles may each comprise at least one tab on the side facing a cartridge opening of each card, the tabs each comprising a part connected to the card and a part raiseable toward said cartridge opening.

The dispenser may further comprise:

the cap comprising at least one cap opening and at least one lid slideable over the cap openings.

The dispenser may be capable of allowing drawing of a top article out through a cap opening.

The dispenser may have each card adhered to a top cover in a stack capable of raising the raiseable part of the tab adhered to a card of an article adjacent below toward the cartridge opening.

The dispenser may have each card configured to bend in the cartridge.

The cartridge may further comprise a platform positioned between the stacks and the springs beneath the stacks, capable of allowing protecting the covers in the stacks from the springs.

The dispenser may include protective elements that are trays, the cap being removable and the dispenser capable of sealing the stacks from the environment outside the cartridge.

Preferably, the trays are flexible.

The dispenser may have a cartridge opening on a wall, the handles each comprising at least one resilient tab facing the cartridge opening of each plate, the trays each comprising a side facing the cartridge opening and a side facing the bottom, the tray further comprising a separator on the side of the tray facing the bottom, the tab capable of sealing the stacks from the environment outside the cartridge, the separator configured to protect a cover from an adjacent article in the stack, and the cartridge being further configured to allow sliding a top tray out of the cartridge.

The dispensers defined above may have a cartridge further comprising holes configured to hold cotton swabs.

Any of the dispensers may include a cartridge further comprising suction pads attached to the cartridge bottom, capable of holding the dispenser immovable during removal of a top skin-adherent cover article from a skin-adherent cover article stack.

Liners may be provided between the skin-adherent material on a cover in a stack, and the adjacent article below.

Each cover may be selected from one or more of the group: skin patch, poultice, plaster and bandage.

According to another aspect of the invention, a method applying a skin-adherent cover is disclosed, the method comprising:

providing a sticky article comprising: a skin-adherent cover, a first and a second handle and a first and a second protective element, the cover comprising: a side comprising skin-adhesive material, an opposite side and edges;

each protective element extending to or beyond all edges of the cover, the first said protective element adhering to the cover opposite side and the second said protective element coupled to the cover side comprising skin-adhesive material, said first handle coupled to the first protective element and said second handle coupled to the second protective element, said first protective element configured to adhere to the cover less than the cover adheres to skin;

pulling the first and second handles apart;

adhering the cover to skin;

employing the first handle to twist the first protective element until detachment of said first protective element from the cover.

Alternatively applying a skin-adherent cover comprises:

providing a sticky article dispenser comprising a cartridge, at least one stack of said articles and at least one resilient element, the cartridge having walls, at least one bottom, at least one cartridge opening and at least one cap configured to snugly cover each cartridge opening; each article comprising: a skin-adherent cover, handle and protective element, the cover comprising: a side comprising skin-adhesive material, an opposite side and edges, the edges facing cartridge walls; the skin-adhesive material being on the side of the cover facing away from a cartridge opening; the handle coupled to the protective element, the protective element attached to the side of the cover facing said cartridge opening, the protective element extending to or beyond all edges of the cover, said protective elements configured to: protect the covers from said walls of the cartridge and adhere to a cover less than the cover adheres to skin; the at least one resilient element within the cartridge positioned in the cartridge below the stacks and configured to urge the skin-adherent articles in the stacks toward said cartridge opening, the dispenser configured to allow removal of a top article from a stack out of said cartridge opening;

pulling the handle of a top article in a stack to remove an article out of said cartridge opening to outside the cartridge;

adhering the cover to skin;

employing the handle to twist the protective element until detachment of said protective element from the cover.

In the application, wherein the sticky article is the top article in a stack of articles, the application may further comprise preparing the articles below in the stack for said application, the preparing comprising providing the second handle of each article above the bottom article in the stack as the first handle of the adjacent article below, such that pulling a first handle of the top article in the stack detaches the cover of the top article from the second handle of the top article and raises the second handle to a position amenable for being pulled.

Alternatively, the application further comprises preparing the articles below the top article in the stack for said application, the preparing comprising pulling the handle of the top article in the stack to raise the handle of the adjacent article below to a position amenable for being pulled.

BRIEF DESCRIPTION OF THE FIGURES

In order to better understand the present invention and appreciate its practical applications, the following Figures are attached and referenced herein. Like components are denoted by like reference numerals.

It should be noted that the figures are given as examples and preferred embodiments only and in no way limit the scope of the present invention as defined in the appending Description and Claims.

FIG. 5A illustrates a side view of the same dispenser, the dispenser containing article stacks, springs and a platform;

FIG. 5B shows a cross sectional frontal view of the same dispenser;

FIG. 5C shows a view of an article including a skin-adherent cover, card and tab;

FIG. 5D shows another view of the article illustrated in FIG. 5C;

FIG. 8A illustrates a side view of the same dispenser, the top article being entirely pulled out of the cartridge;

FIG. 8B shows a cross sectional frontal view of the same;

FIG. 13A illustrates a side view of an article dispenser including trays, and suitable for drawing of a top article up through an upper opening;

FIG. 13B shows a perspective view of the dispenser including trays;

FIG. 16 shows a view in perspective of an article dispenser including trays, and suitable for drawing of a top article by sliding it out through an upper opening;

DETAILED DESCRIPTION OF THE EMBODIMENTS

Figure 1:
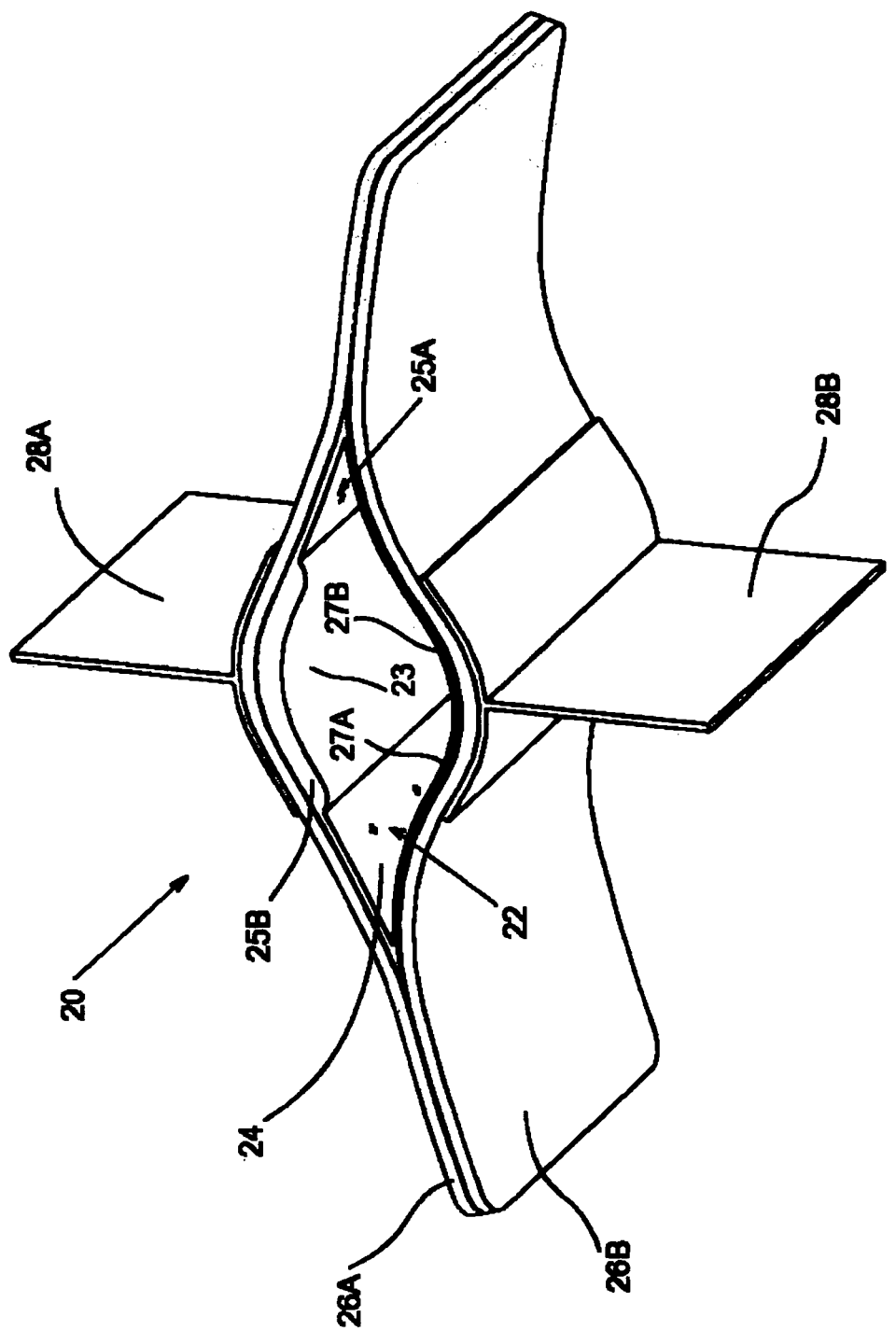
FIG. 1 illustrates a sticky article comprising: a skin-adherent cover, a first and a second handle and a first and a second protective element, the cover comprising: a side comprising skin-adhesive material, an opposite side and edges.

The adhesive article embodiments described hereinbelow provide individual skin-adherent covers ready to be immediately adhered onto a wound in a simple way.

The adhesive skin-adherent covers are similar to an ordinary type as far as having a surface of skin-adhesive material on one face of the skin-adherent cover, but include other novel features.

Liners such as thin films of paraffin or PTFE may cover at least the skin-adhesive material until close to the time the skin-adherent cover is applied to the affected area, as in commercially available plasters for example.

However, one of the advantages of the adhesive skin-adherent covers suitable for use in the embodiments is that in contrast to some commercially available skin-adherent covers, it is exceedingly easy to remove wrapping on the skin-adherent covers prior to application to skin, with minimal risk of accidental contact with any part of the cover on the side that includes the skin-adhesive material, and with minimal exposure of the unwrapped cover to the environment thanks to the amenability to quick and easy manipulation of the articles.

Some embodiments further allow easy packing and unpacking the skin-adherent covers from dispensers, and/or applying the skin-adherent covers, while easily keeping the skin-adherent cover sides untouched throughout.

Some embodiments also allow easily removing self-peeling liners off skin-adherent covers during the unpacking of the skin-adherent covers from the dispensers.

Articles including easily-applied covers have the following common features: a skin-adherent cover, at least one handle and at least one protective element, in which the cover includes: a side comprising skin-adhesive material, an opposite side and edges.

Each protective element is protective of the cover from mechanical damage, warping from environmental conditions etc., and each protective element extending to or beyond all edges of the cover, and adhered to the cover opposite side.

The handle is coupled to the protective element.

The protective element is configured to adhere to the cover less than the cover adheres to skin.

Another protective element and another handle are situated to the side of the cover that includes the skin-adhesive material, such that pulling a handle coupled to the opposite side easily detaches the coupled cover from the protective element and handle situated to the side of the cover that includes the skin-adhesive material.

In addition to the embodiments having the common features described above, which will be described in greater detail below for several embodiments, the embodiments allow easily applying the covers to skin by for example adhering the cover (still coupled on the opposite side to a protective element and to a handle) to skin, and employing the handle to twist the protective element until detachment of said protective element from the cover.

In some embodiments, the articles may be provided as individual units, which may for example be individually purchased, or for example a quantity may be purchased as freely dispersed individuals in a bag.

Alternatively, the articles may be provided along with a dispenser, which again may store them freely dispersed, or alternatively arranged in the dispenser, for example in stacks.

In some embodiments, a tab (handle) which is used for pulling an article out of the dispenser is also an element that protects the adhesive part of the article above it in the stack.

The dispensers may provide additional protection to the covers. Such protection may include mechanical protection, protection from environment (for example precipitation, heat and/or sunlight), as well as maintain cleanliness or even sterility.

An individual article including a cover is shown in perspective in FIG. 1. The sticky article 20 comprises: a skin-adherent cover 22, a first 28A and a second 28B handle and a first 26A and a second 26B protective element.

The cover 22 comprises: a side 25A comprising skin-adhesive material 24, an opposite side (not shown) and edges (only one edge 25B visible in the figure).

The protective elements 26A, 26B are protective of the cover 22, each protective element 26A and 26B extending to or beyond all edges of the cover 22, the first said protective element 26A adhering to the cover opposite side and the second said protective element coupled to the cover side 25A comprising skin-adhesive material 24.

The first handle 28A is coupled to the first protective element 26A, and the second handle 28B is coupled to the second protective element 26B.

The first protective element 26A is configured to adhere to the cover 22 less than the cover 22 adheres to skin (not shown).

The article 20 is typically provided with protective elements 26A and 26B in intimate contact with each other, preferably adhered to each other. FIG. 1 shows the article in a state wherein the protective elements 26A, 26B are partially apart to demonstrate that the article is configured to allow detachment of said second element 26B and second handle 28B from said cover 22 when said first 28A and second 28B handles are pulled apart, for example by firmly holding each handle between fingers of a hand and pulling the handles in opposite directions.

The article 20 also includes liners 27A, 27B non-adherently contacting the skin-adhesive material 24. Such liners may prevent contact of the protective element 26B with the skin-adhesive material 24. They may also help maintain cleanliness or sterility of a pad 23 on the cover 22, for example in sterile plasters.

Figure 2A:
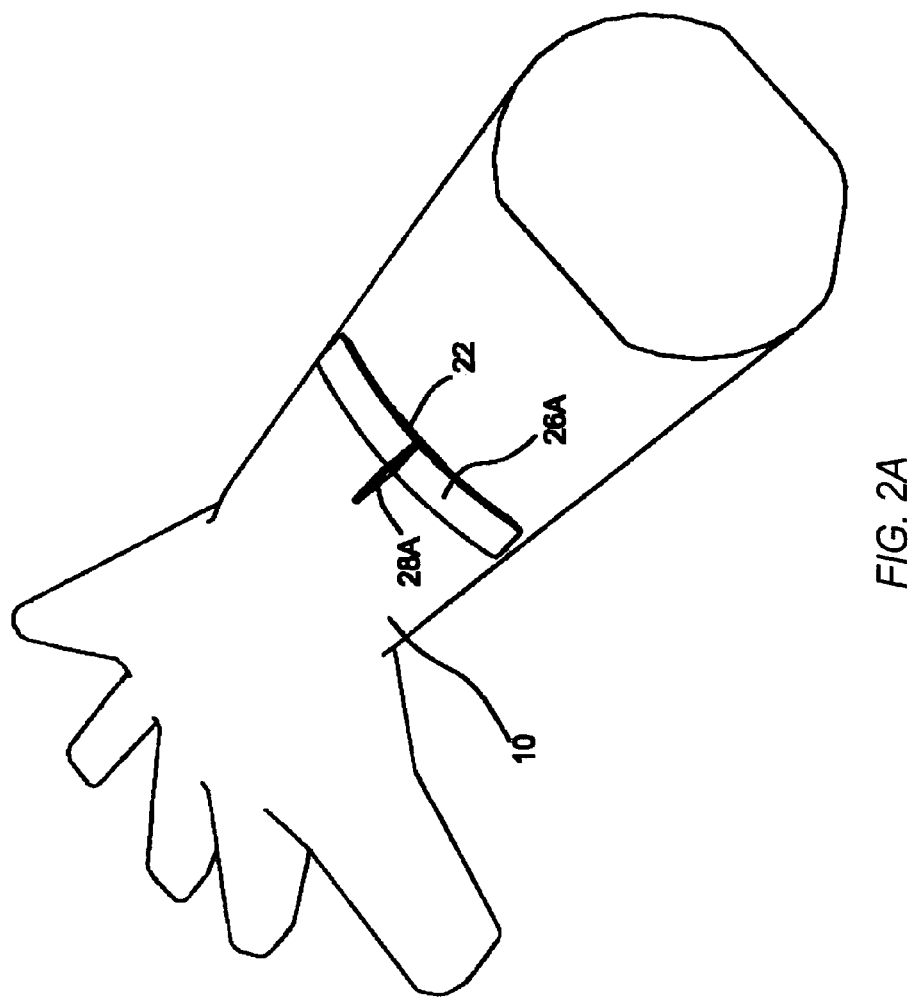
FIG. 2A shows first stage application of the cover to skin.
Figure 2B:
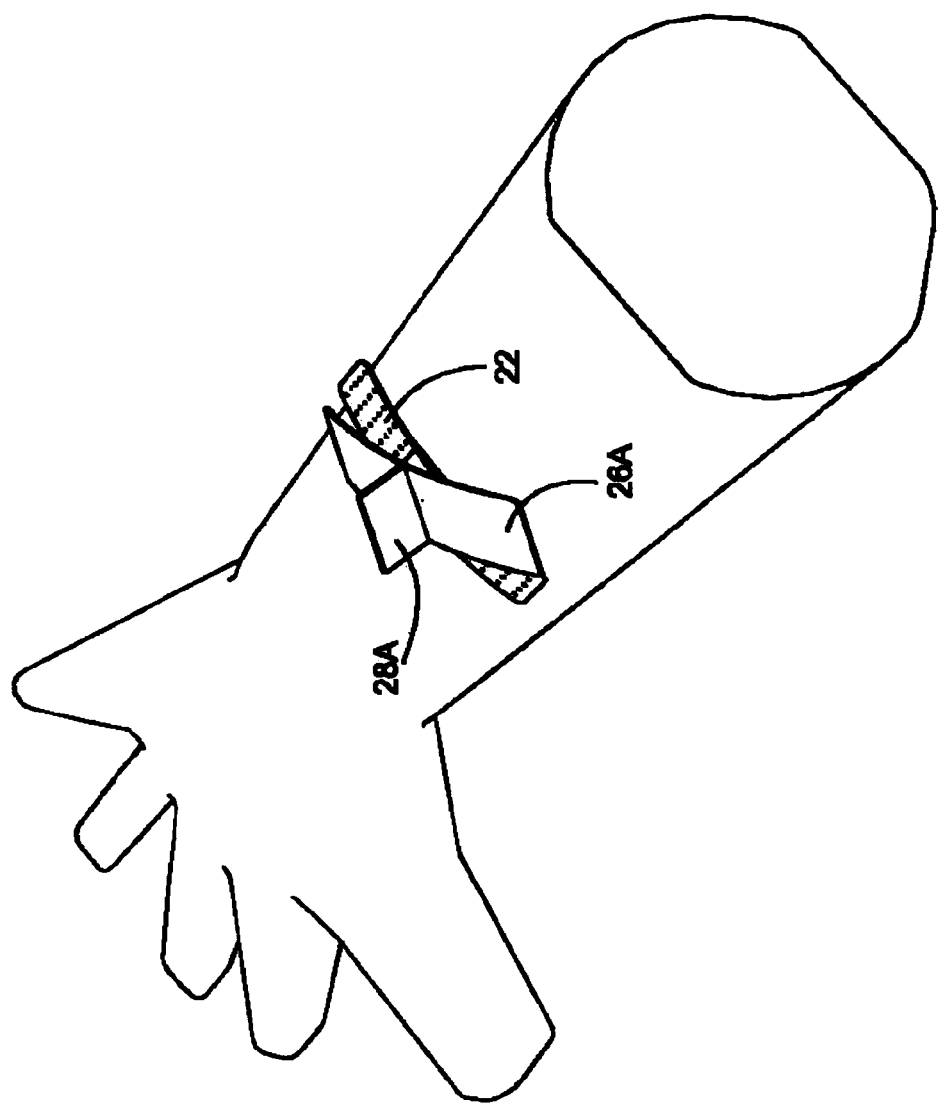
FIG. 2B shows the next stage of the application, in which the first handle is twisted.
Figure 2C:
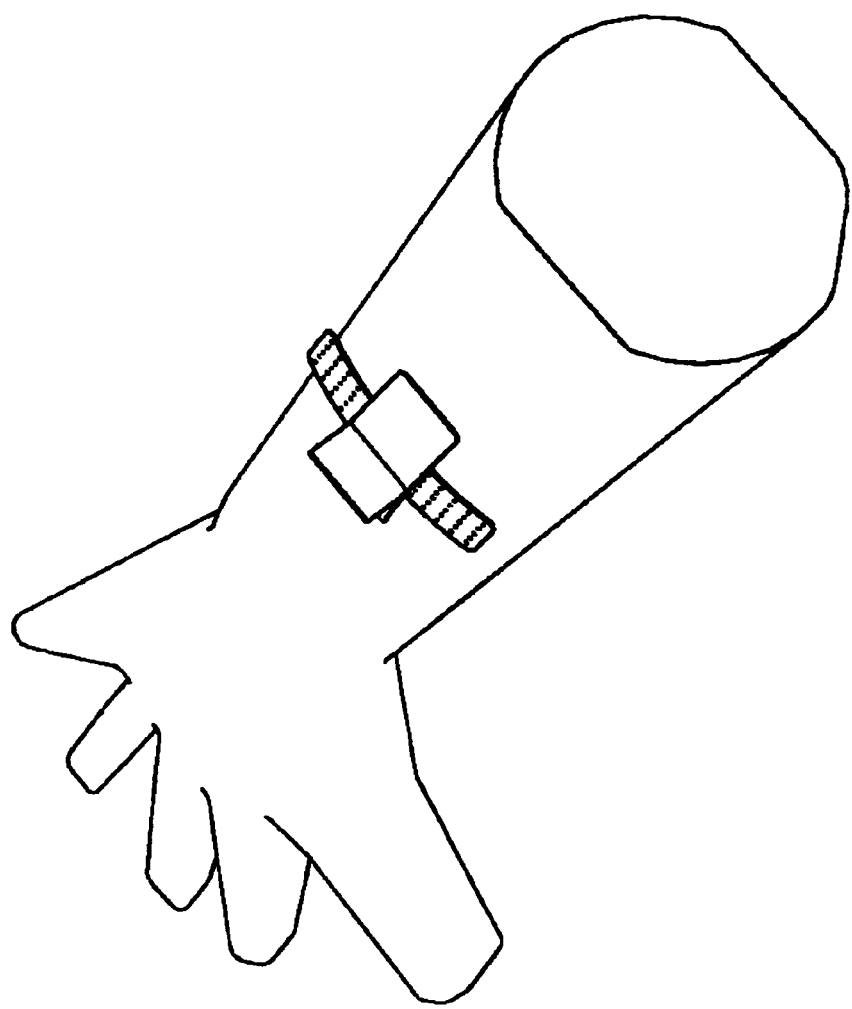
FIG. 2C shows the completion of the twisting stage.
Figure 2D:
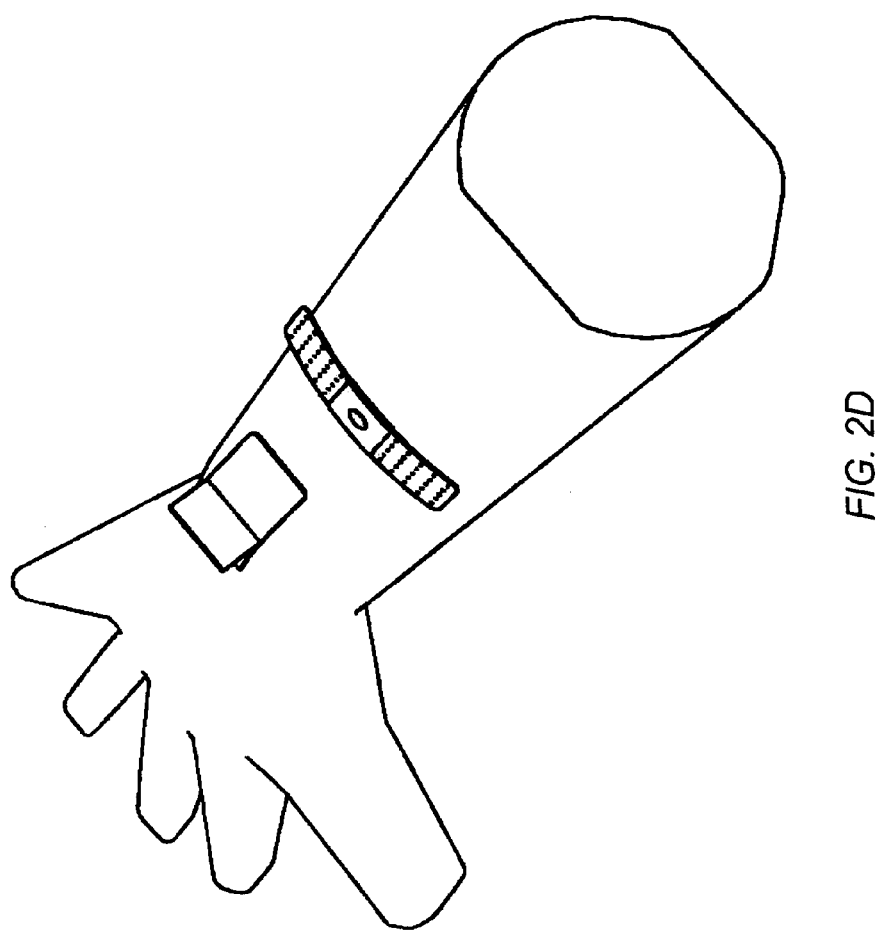
FIG. 2D demonstrates removal of the first handle and the first protective element from the skin.

As shown in FIGS. 2a-2D, applying the cover 22 after pulling the first 28A and second handle (not shown) apart includes:

adhering the cover 22 to skin 10, FIG. 2A;

employing the first handle 28A to twist the first protective element 26A (FIGS. 2B and 2C) until detachment of said first protective element 26A from the cover 22 (FIG. 2D).

The dispenser embodiments described hereinbelow have the following common features:

A cartridge, at least one stack of articles and at least one resilient element.

The cartridge has walls, at least one bottom, at least one opening and at least one cap configured to snugly cover the openings.

Each article comprises: a skin-adherent cover, handle and protective element, the cover comprising: a side comprising skin-adhesive material, an opposite side and edges, the edges facing cartridge walls;

the skin-adhesive material being on the side of the cover facing away from an opening;

the handle coupled to the protective element, the protective element attached to the side of the cover facing said opening;

the protective element extending to or beyond all edges of the cover, said protective elements configured to:

protect the covers from said walls of the cartridge;

adhere to a cover less than the cover adheres to skin;

the at least one resilient element within the cartridge positioned in the cartridge below the stacks and configured to urge the skin-adherent articles in the stacks toward said opening, the dispenser configured to allow removal of a top article from a stack out of said opening.

In addition, all the dispensers described below are configured to seal the skin-adherent covers from the environment outside the cartridge and to protect a cover from an adjacent article in the stack.

Figure 3B:
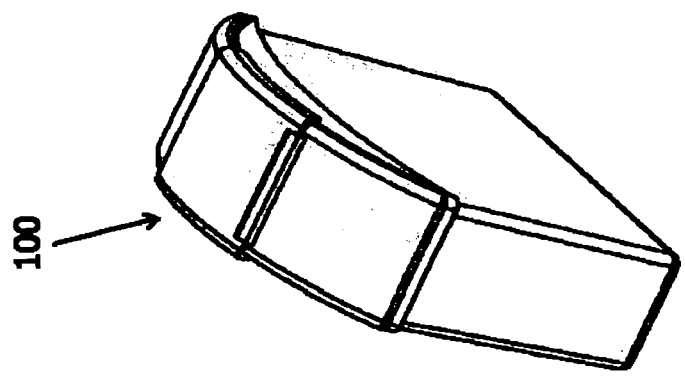
FIG. 3B shows another perspective view of the same.
Figure 3A:
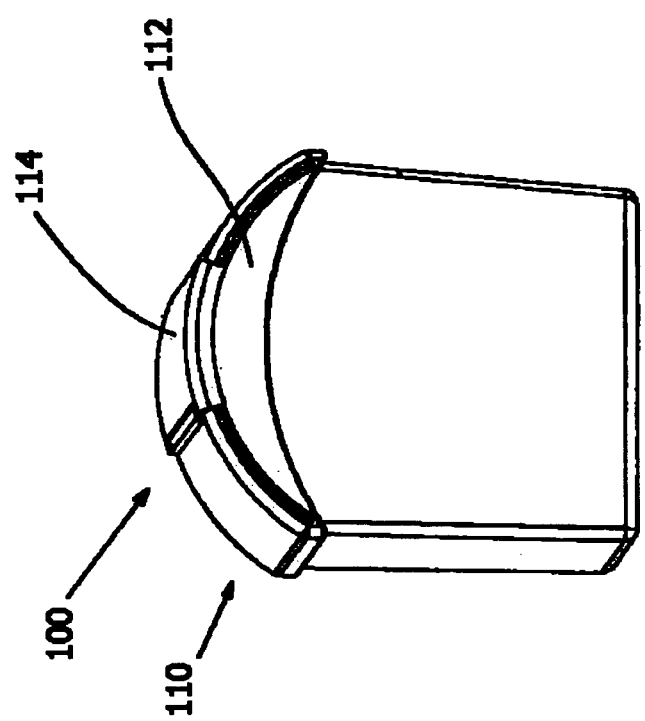
FIG. 3A illustrates an elevated perspective view of a closed dispenser having a cartridge with skin-adherent covers attached to flexible cards within.

Reference is made to FIG. 3 illustrating elevated perspective view of a closed dispenser 100 in accordance with one embodiment.

The cartridge 110 includes a cap 112 that has an opening (not shown) covered by a slideable lid 114.

The lid 114 is shown as closing the opening, which is the preferred position of the lid 114 when the dispenser 100 is not in use, in order to isolate the interior of the cartridge 110, containing covers such as sterile bandages, from the environment outside the cartridge.

Figure 4B:
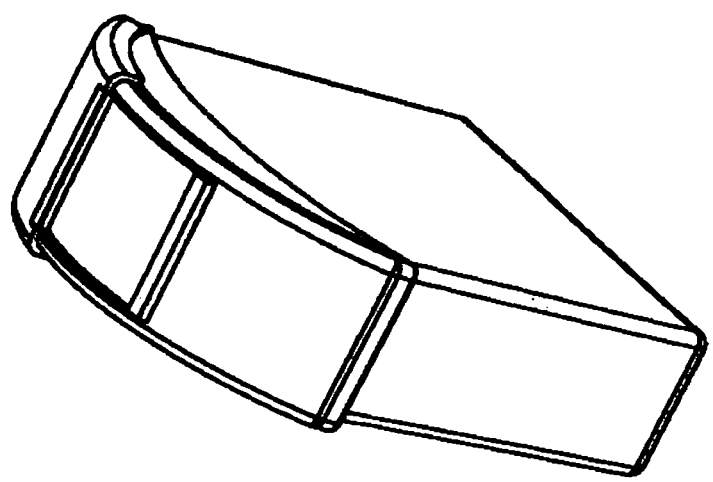
FIG. 4B shows another perspective view of the open dispenser.
Figure 4A:
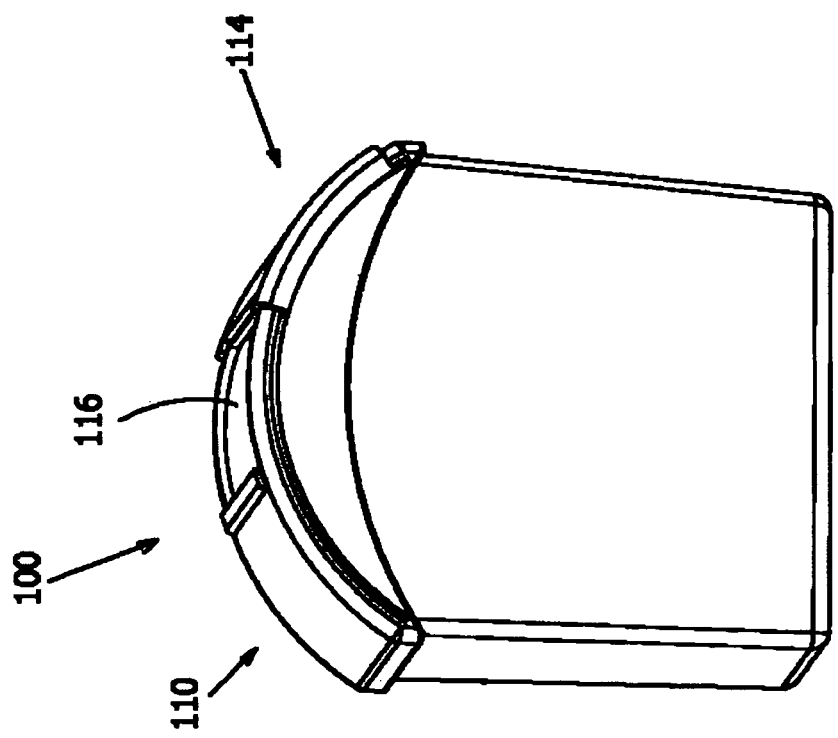
FIG. 4A illustrates an elevated perspective view of the same dispenser open.

FIG. 4 shows open dispenser 100 in perspective view. The view is at angles identical to those of FIG. 3. Lid 114 is slid all the way back to the right, exposing upper opening 116.

FIGS. 5A and 5B illustrate a side view and a cross sectional frontal view, respectively, of the article dispenser 100, with the lid 114 slid back as in FIG. 4. The cartridge 110 includes walls 115 (two of the four walls being shown in FIG. 5B), upper opening 116 and bottom 117.

Plurality of articles 120 are organized as a stack 121 within cartridge 110.

FIGS. 5C and 5D show two views of an article 120 including a bandage 122, card 126 and tab 128, suitable for installation in dispenser 100.

Each article 120 as shown in FIGS. 4C and 4D is provided with an adhering bandage 122 shown in FIGS. 4b and 4c that is placed beneath card 126. Card 126 is a protective element that helps prevent damage or disfigurement of the bandage 122. One side of adhesive bandage 122 is provided with a pad 123 substantially in the center of adhesive bandage 122 and adhesive material 124 that covers the area of bandage 122 that surrounds pad 123. The side is adherable onto an area of skin.

Another, opposite side of adhesive bandage 122 is provided with an adhering material adhering the adhesive bandage 122 to card 126. This side is outwardly placed when the bandage 122 is applied to the body.

The upper side of card 126 is glued to a tab 128. Tab 128 acts as a handle by which the top skin-adherent cover 120A may be removed from the dispenser 100.

The dispenser 100 also includes springs 130, resilient elements that urge the articles 120 toward upper opening 116, and a platform 140 positioned between the bottom article 120B and the springs 130, capable of allowing urging of the articles 120 toward the upper opening 116 and protecting the skin-adherent covers 122 from the springs 130.

As long as there are articles 120 in the cartridge 110, the tab 128A of top article 120A will be positioned in upper opening 116.

Figure 6B:
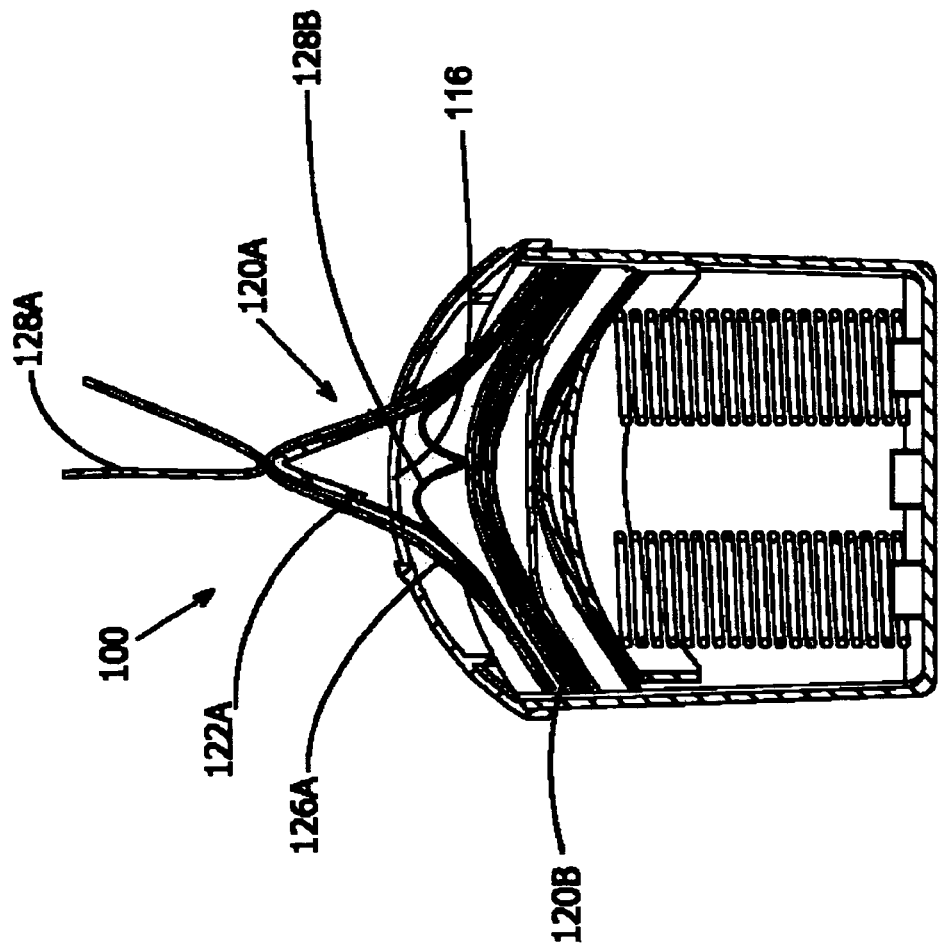
FIG. 6B shows a cross sectional frontal view of the same.
Figure 6A:
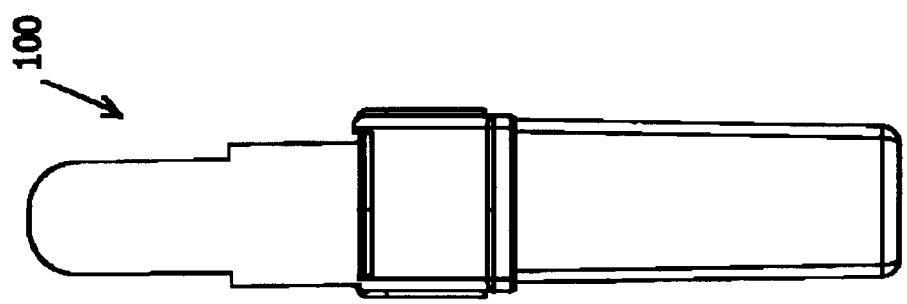
FIG. 6A illustrates a side view of the same dispenser, a top article being partially pulled out of the cartridge.

Reference is now made to FIGS. 6A and 6B illustrating a side view and a cross sectional frontal view respectively of the dispenser 100 shown in FIGS. 4 and 5 during the process of pulling a top article 120A out of the dispenser 100.

When a user wants to place an adhesive skin-adherent cover 122A onto a wound, she pulls tab 128A that is attached to the top of card 126A and protrudes through opening 116. As article 120A rises through opening 116, card 126A is compressed by the sides of the opening 116, so that the sides of the card 126A (the left and right sides in FIG. 6B) are drawn towards each other, dragging upwards the tab 128B of the article 120B under the top article 120A.

Figure 7B:
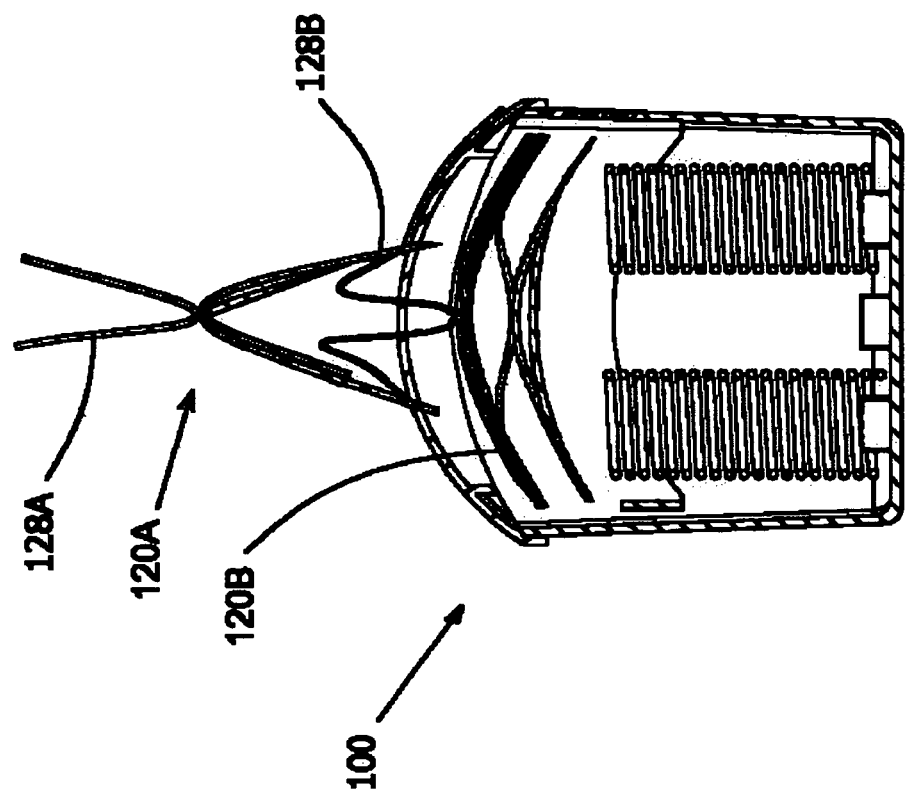
FIG. 7B shows the same from a cross sectional frontal view.
Figure 7A:
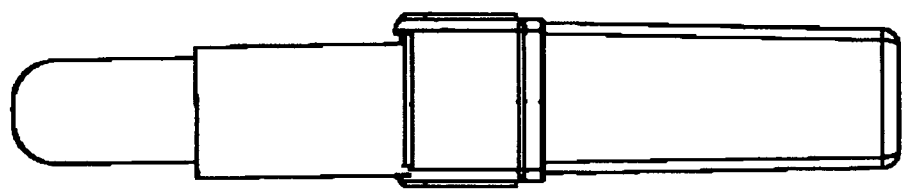
FIG. 7A illustrates a side view of the same dispenser, the top article being further pulled out of the cartridge.

As shown in FIG. 7, further pulling the top tab 128A straightens the edges of the tab 128B underneath. Upon full withdrawal of the top article 120A, as shown in FIG. 8, the article 120B underneath becomes the top article in the cartridge 110, tab 128B having the same form as the former tab 128A had when its article 120A was top article in the cartridge 110.

Card 126B now blocks opening 116, which may suffice to protect the bandages 122 (or in other embodiments plasters, skin patches etc) from contamination. The pad 123 and optionally the adhesive material 124 surrounding the pad 123 may additionally be covered with a liner (not shown) to further help maintain the sterility of the pad 123 and optionally help separate the pad 123 from articles 120 below it.

Tab 128 may be made of resilient yet stiff material, which allows pushing the top tab 128A back into the cartridge 110 under the upper opening 116, to allow closing of the lid 114 over the opening 116, to help protect the bandages 120 from damage and from contamination. Upon sliding the lid 114 back again, the top tab 128A preferably pops back up to its former raised position.

The top article 120A in each stack 121 may be provided with the tab already raised, to ease first use of the dispenser.

Figure 9B:
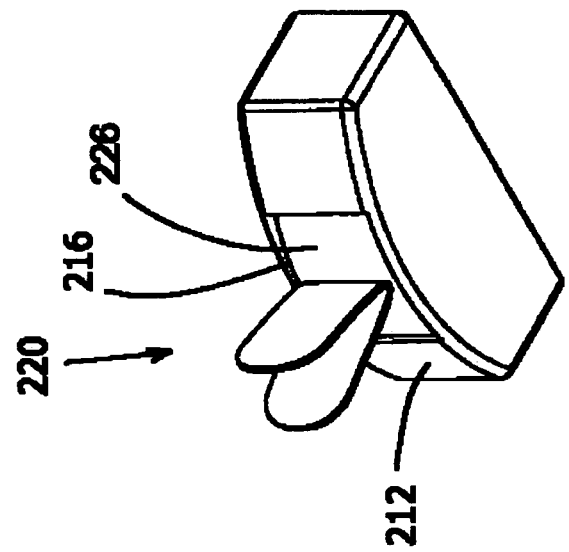
FIG. 9B shows a perspective view of the same dispenser.
Figure 9A:
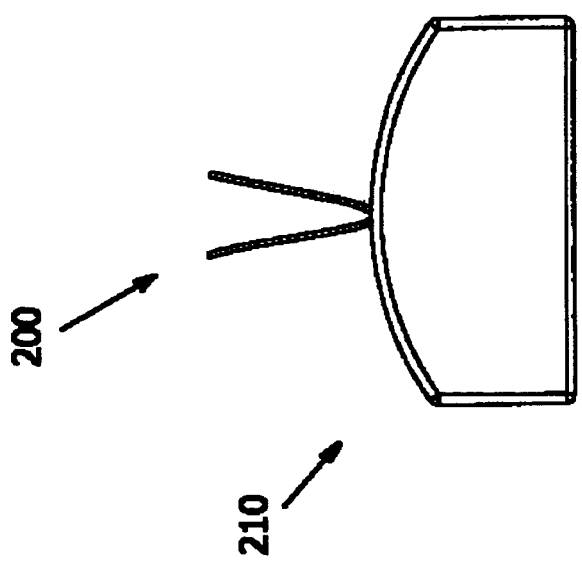
FIG. 9A illustrates a side view of a dispenser with skin-adherent covers attached to flexible cards within, the dispenser not containing springs nor platform.

FIGS. 9A and 9B show a side view and a perspective view, respectively, of another embodiment, a dispenser 200 also having articles 220 with cards 226. Compared to the dispenser 100 described above, this dispenser 200 has a more compact cartridge 210 with lower walls.

Figure 10:
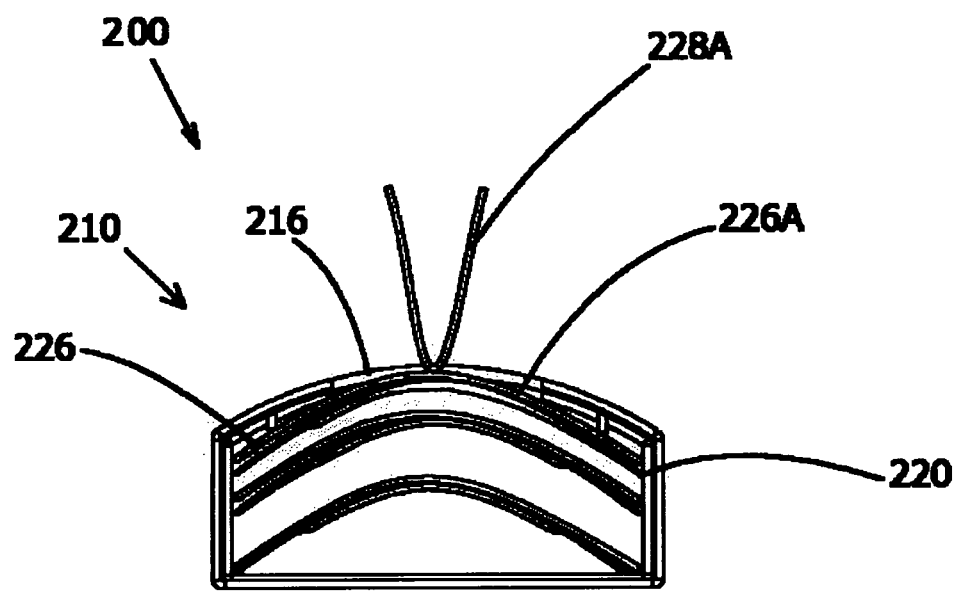
FIG. 10 shows a cross sectional frontal view of the same dispenser, the top article being partially pulled out of the cartridge.

FIG. 10 depicts a cross sectional frontal view of the dispenser 200. Due to the relatively low walls of the dispenser 200, the dispenser 200 holds relatively few articles 220. Therefore, resilient cards 226, bent in the cartridge 210 upwards toward the opening 216, may have sufficient force to urge the articles 220 up, sufficiently to expose the top tab 228A out of opening 216 and let the top card 226A block the opening 116. A spring may not be required to help urge the articles 220 upwards, and a platform is consequently also not required.

Figure 11:
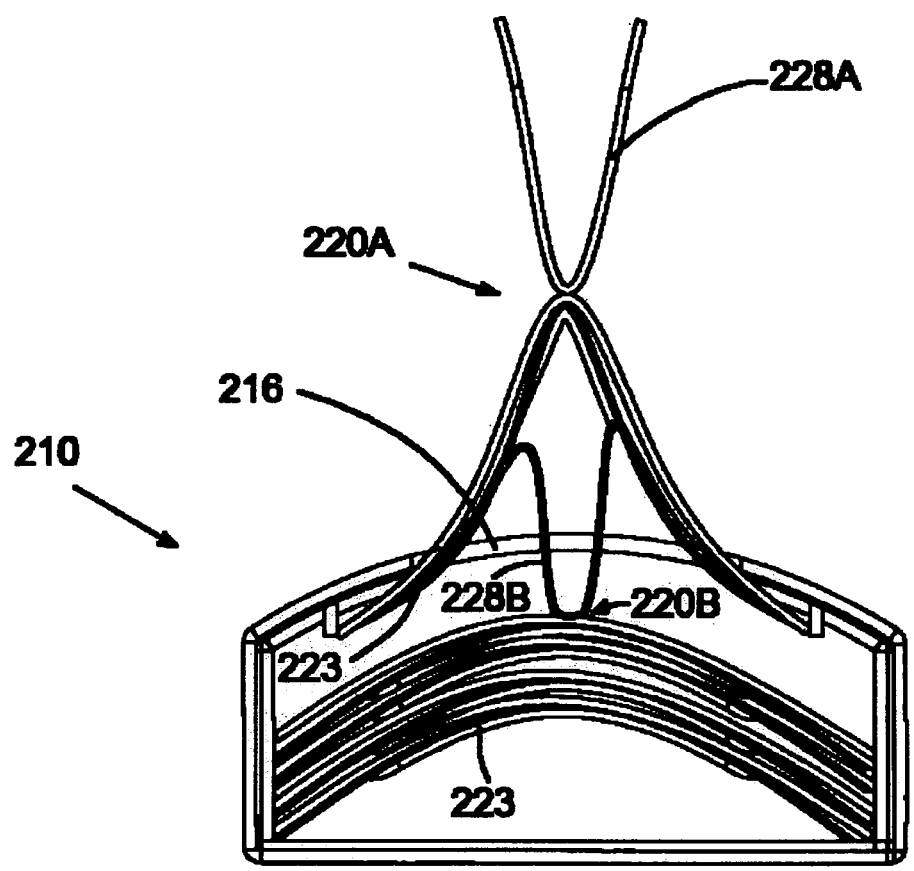
FIG. 11 shows a cross sectional frontal view of the same dispenser, the top article being further pulled out of the cartridge.
Figure 12:
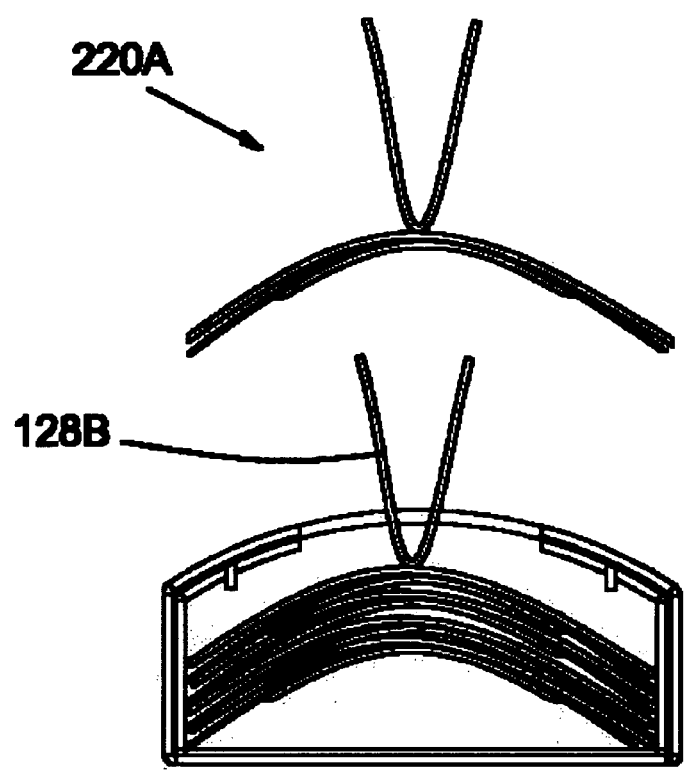
FIG. 12 shows a cross sectional frontal view of the same dispenser, the top article being entirely pulled out of the cartridge.

As shown in FIGS. 11 and 12, similar to the formerly described dispenser 100, pulling a top tab 228A so that a top article 220A is drawn out of the dispenser 210 brings about pulling out of a second tab 128B on an article 220B underneath the top article 220A. It is notable that the tension applied during the withdrawal of the top article 220A may substantially assist in moving the article 220B underneath up towards the opening 216.

A dispenser 200 may be prepared by adhering a card 226 to each cover 222 on the side opposite the side with skin-adhesive material, extending the card 226 beyond all sides of the s cover 222 to protect the cover 222 from the walls of the cartridge 210; partially connecting at least one tab 228 to each card 226, to the face of the card 226 away from the side of the card adherent to a skin-adherent cover 222, leaving a part of the tab 228 raiseable; and placing articles 220 in stacks 221 in the cartridge 210 with the skin-adhesive material 223 exposed in a direction away from the upper opening 216.

In embodiments wherein the covers are sterile, all of the dispenser components may be sterile during packing the dispenser. After packing the dispenser a snugly fitting cap may be placed over the upper opening, after which the dispenser may be used under non-sterile conditions, the dispenser being configured to maintain the sterility of the covers.

It is notable that in some embodiments the tabs may be simply coupled to the covers above them in the stacks. The mere contact of the covers with the tabs is sufficient to enable raising the tabs of the articles when the articles above them are removed from the cartridge. Alternatively, the covers may be lightly adhered to the tabs below them in the stack.

Furthermore, some embodiments (not shown) may not include a cartridge, the embodiments consisting of stacks of articles only. In such embodiments the covers are typically lightly adhered to the tab of an adjacent article in the stack.

Generally speaking, the definition of an article in a stack of articles not in a cartridge can be similar to the definition of the individual article described in FIG. 1 and above: an individual article comprises: a skin-adherent cover, a first and a second handle and a first and a second protective element.

Looking at a stack of articles positioned as in the stacks described in FIGS. 5-12 and above, namely the first handle and first protective element is above the cover and the second handle and second protective element are below the cover, the stack can be defined as follows: the second handle of each article above the bottom article in the stack is the first handle of the adjacent article below.

FIGS. 13A and 13B illustrate a side view and a perspective view, respectively, of a skin-adherent cover dispenser 300 in accordance with another embodiment. In this embodiment, the protective elements are flexible trays 326, and a cartridge 310 includes a removable cap 312, the removed cap 312 capable of allowing drawing of a top article 320A out through the upper opening 316. The cap 312 may be connected via a hinge to the dispenser 310.

Figure 14A:
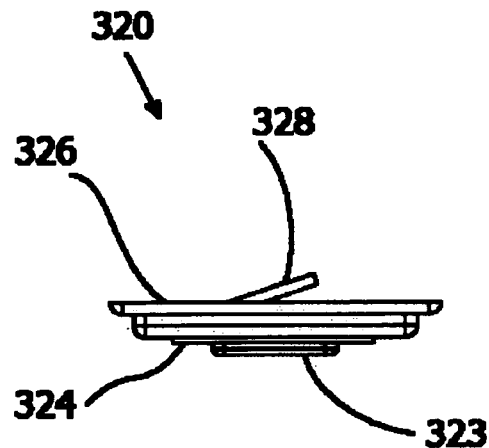
FIG. 14A show an enlarged side view of an article including tabs, tray and tabs having a raiseable part, suitable for the dispenser shown in FIGS. 13A and 13B.
Figure 14B:
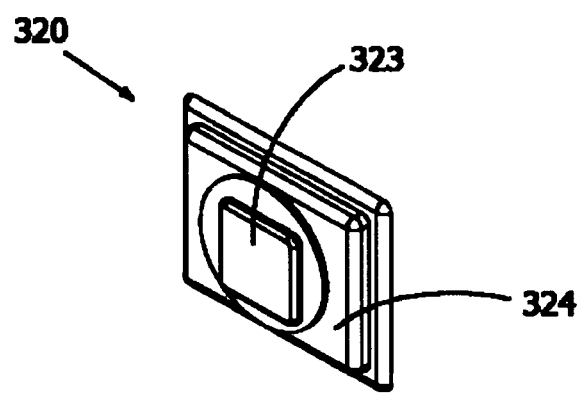
FIG. 14B shows a perspective view of the article including tabs and tray.

As shown in an enlarged view in side view and perspective views of an article 320, FIGS. 14A and 14B respectively, the handles are tabs 328 one of each tray 326, the tabs 328 each having a part connected to the tray 326 and a raiseable part. A bandage 322 is adhered to the second, opposite side of side of tray 326, the bandage 322 including a sterile pad 323 and a skin-adhesive part 324.

Returning to FIGS. 13A, 13B, the bandages 322 (and coupled trays 326 and tabs 328) may be sufficiently small to allow placing more than one stack 321 of articles 320 in the cartridge 310. The articles 320 are placed in the cartridge 310 with the skin-adherent material 323 facing away from the upper opening 316.

A top article 320A may be removed from the dispenser 300 by first removing the cap 312 and pulling up a tab 328A of a top article 320A, see the top right tab 328A in FIGS. 13A, 13B. Alternatively to raising the tab 328A with a finger for example, the tabs 328 may be resilient, so that the tab 328A automatically rises when the article above the tab is withdrawn from the cartridge.

FIGS. 15A-15E show additional views of the dispenser 300 and its components.

Figure 15C:
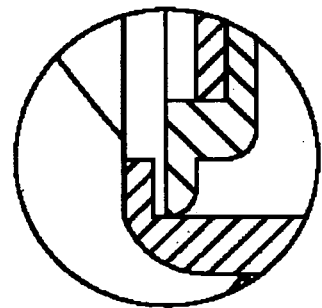
FIG. 15C shows the same in an exploded view.
Figure 15E:
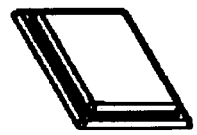
FIG. 15E shows a second perspective view of the article.
Figure 15D:
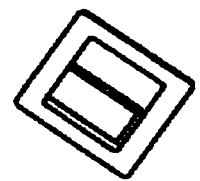
FIG. 15D shows a first perspective view of the article.
Figure 15B:
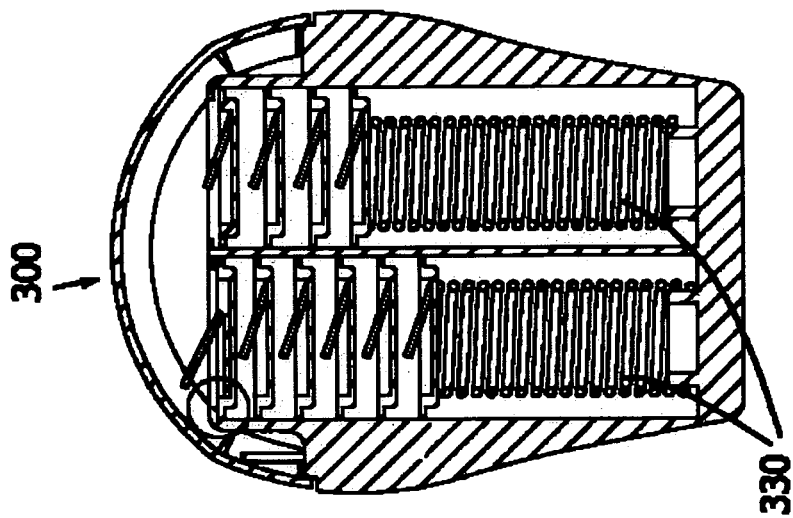
FIG. 15B shows a cross sectional frontal view of the same.
Figure 15A:
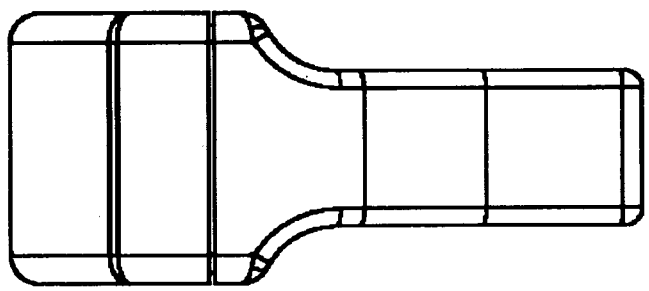
FIG. 15A shows a side view of the same dispenser, having two stacks of articles held over springs.

As shown in the cross sectional frontal of the dispenser 300 in FIG. 15B, a coiled spring 330 is placed between the bottom of the cartridge 310 and the bottom article in each stack 321 of articles 320 in the cartridge 310. The size of the upper opening 316 as well as the size of the trays 326 may be designed such that the spring 330 forces the trays 326 against the cartridge, as shown in the exploded view in FIG. 15C, thus sealing the b 322 from the environment. Removal of the articles 320 is possible due to the flexibility of the trays 326 as well as the sizes of the opening 316 and the trays 326, which allow squeezing the trays 326 through the opening 316 by pulling the tabs 328, which sufficiently bend the attached trays 326 to get through. On the other hand, the trays are configured to protect the attached bandages (not shown in FIGS. 15A-15E). The adhesive skin-adherent cover of the removed article 320A (FIG. 13A) is applied by pressing the tray to the skin, by either holding onto the tab 328A or directly onto tray 326A. Suitable materials for construction of the trays may be plain laminated cardboard or polycarbonate or ABS for example.

Yet another dispenser 400 is shown in FIG. 16, in which wherein the protective elements are trays 426 and the cap 412 is removable, the removed cap 412 capable of allowing drawing of a top bandage for example (not shown) out through the upper opening 416.

Tracks 418 proximal to upper opening 416 are capable of holding and allowing sliding a tray 426 adhered to a bandage in a stack of articles out of the cartridge 410.

Figure 17A:
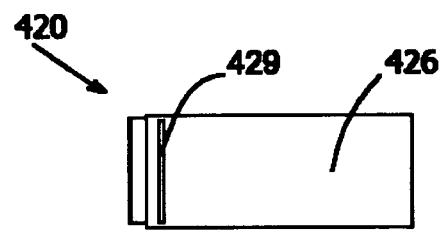
FIG. 17A shows a top view, of an article suitable for the dispenser shown in FIG. 16.
Figure 17B:
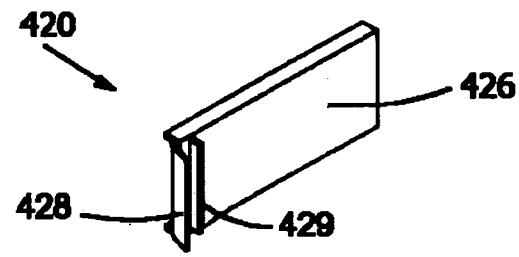
FIG. 17B shows a side view of same.
Figure 17C:
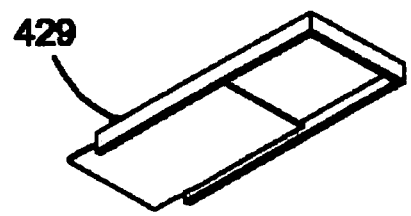
FIG. 17C illustrates a perspective view of the same.

FIGS. 17A, 17B and 17C show a top view and top and bottom perspective views, respectively, of an article 420 including a, a tray 426, a separator 429 and a tab or handle 428. The tab 428 has a part exposed beyond one end of the tray 426, the skin-adhesive part of the bandage allowing attachment of the top bandage to skin.

Figure 18C:
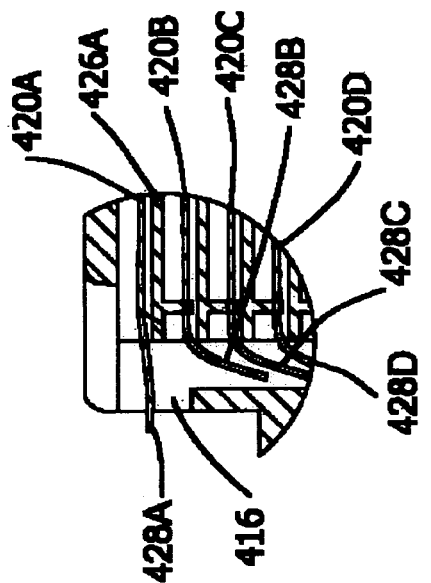
FIG. 18C shows an exploded view of the same.
Figure 18B:
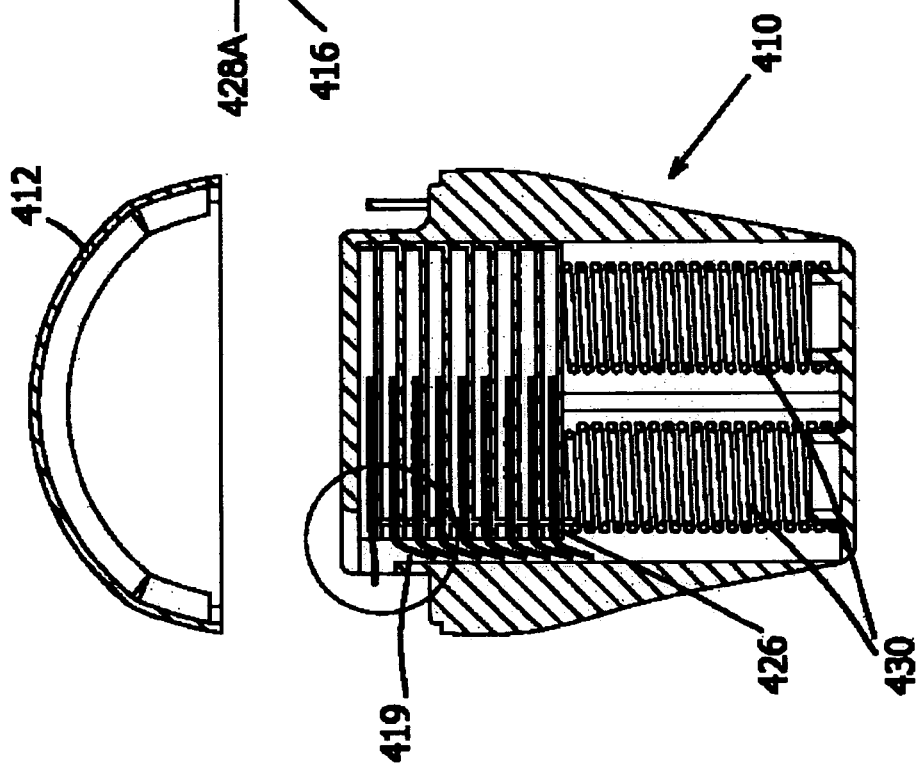
FIG. 18B shows a cross-sectional frontal view of the same.
Figure 18A:
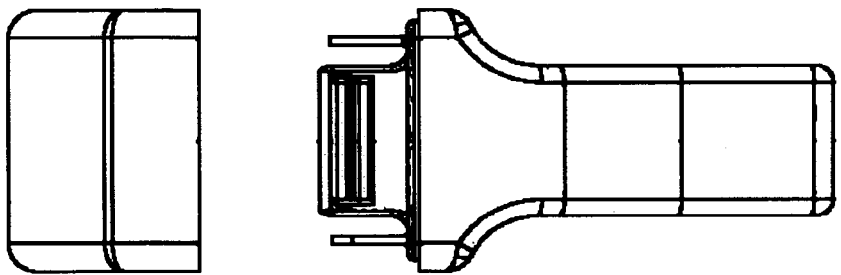
FIG. 18A shows a side view of the same dispenser.

FIGS. 18A, 18B and 18C show a side view, a cross-sectional frontal view and an exploded view of the dispenser 400.

Springs 420 are provided within cartridge 410 and beneath plurality of articles 420 that urge the articles 420 up towards opening 416 of the cartridge. The top article 420A will be positioned exposed to opening 416.

Note that under the articles and above the spring 430 there may be a bottom tray 426 without a skin-adherent cover attached to it, since the tray is in direct contact with a spring 430. Alternatively, the separator 429 may be configured to sufficiently distance the spring 430 from the bottom cover and allow placing a bandage or other cover under the bottom article 420.

The trays 426 are preferably sized to be slidingly held in tracks 418. Trays 426 are sized and placed in the cartridge 410 so that when placed therein in a stack, as clearly shown in FIG. 18B, a gap 419 remains between them and the wall on which the upper opening 416 is positioned. In addition, articles 420 are placed in the cartridge 410 with the part of the tab 428 extending beyond one end of the tray 426, facing the wall of the cartridge 410 on which there is the opening 416. With this arrangement of dispenser 400, as shown in FIGS. 18B and 18C, the exposed parts of the tabs 428 are slightly bent within the cartridge 400, providing a seal that prevents or helps to prevent contamination of the bandages. The top article 420A, being partly exposed in opening 416, is not bent and thus is accessible for withdrawal when the cap 412 is removed.

Each article 420 seals and protects the article 420 below it. To use a top article 420A, a user may pull the exposed tab 428A of the top article 420A to help slide the article 420A out of the upper opening 416, to provide better accessibility for a user to the bandage.

As shown in FIG. 13A, the dispenser cartridges may further be provided with a plurality of holes 350 for holding swabs 354.

The buds of the swabs may be dipped in an anti-infection material so that the user, before applying the skin-adherent cover, can clean or disinfect the wound.

The cartridges may further have suction pads (not shown) attached to the cartridge bottoms, capable of holding the dispensers immovable during removal of a top skin-adherent article from a skin-adherent cover article stack.

Figure 19:
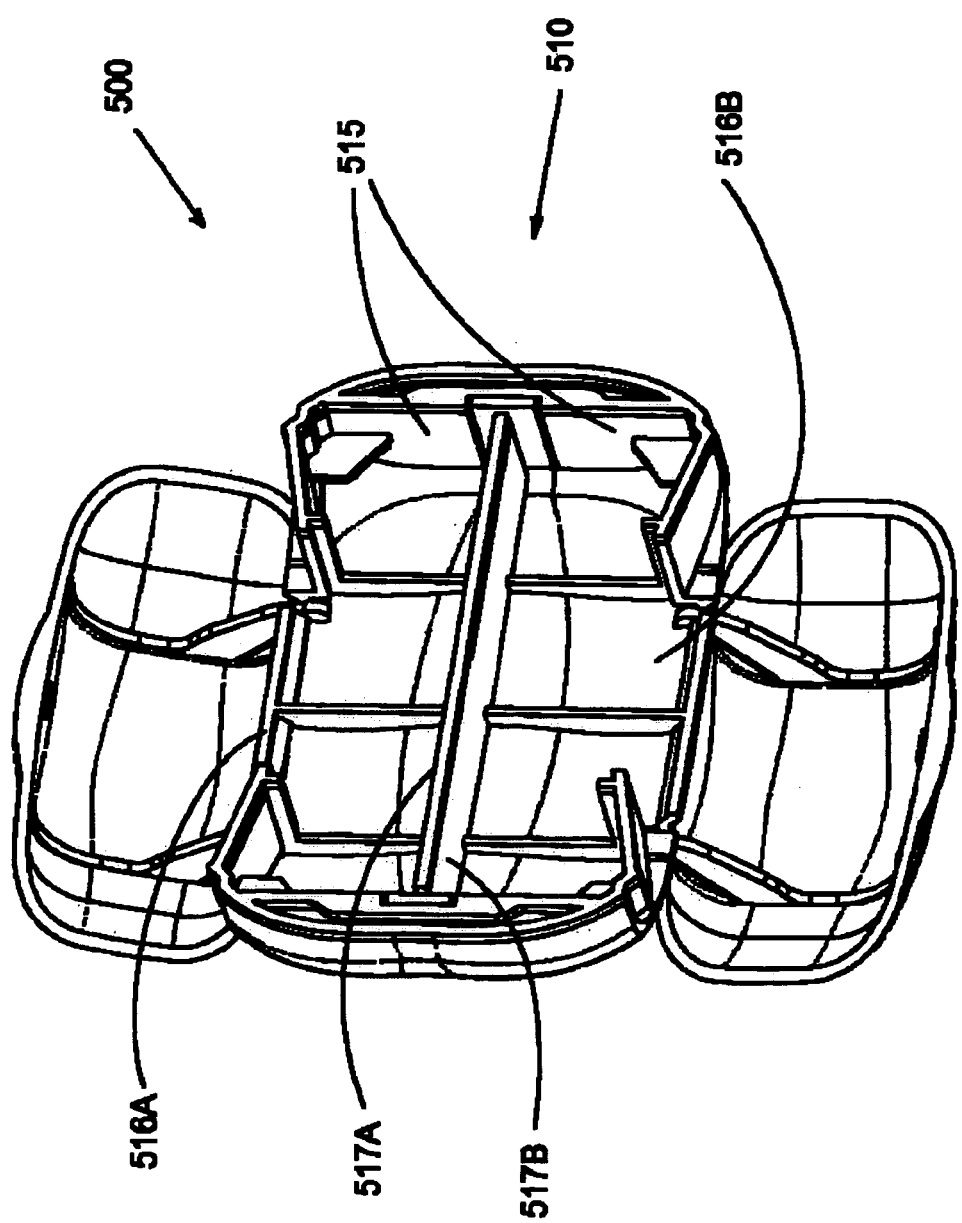
FIG. 19 shows an isometric view of an opened dispenser with double openings for dispensing sticky articles.

FIG. 19 shows an isometric cross-sectional view of a dispenser 500 including a cartridge 510 with double openings 516A, 516B for dispensing sticky articles.

The cartridge 510 is similar to the cartridge 210 shown in FIGS. 9A and 9B in all respects. The other dispensers described above may be similarly modified to provide multiple openings for dispensing covers.

Notably, in such multi-compartmented embodiments there is no "up" and "down", However, for the sake of simplicity, the embodiments above which do have just one opening (and bottom) were described in terms of "up" and "top" and "low" or "bottom".

The cartridge 510 thus has walls 515, openings 516A, 516B, and bottoms 517A and 517B.

Figure 20:
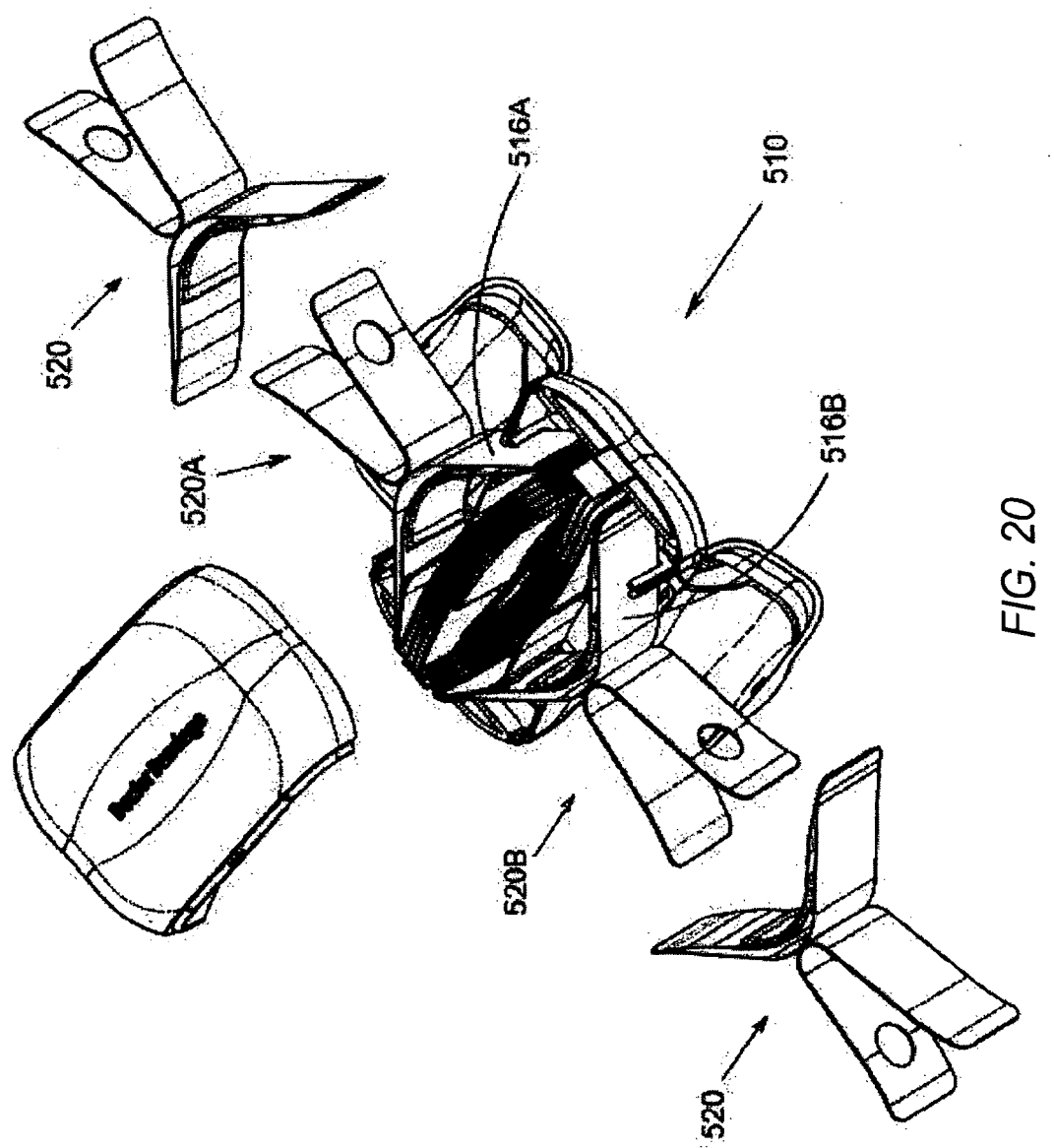
FIG. 20 illustrate an isometric exploded view of an opened dispenser with double openings with stored as well as dispensed sticky articles.

FIG. 20 illustrate an isometric exploded view of an opened cartridge 510 with double openings 516A, 516B, with stored as well as dispensed sticky articles 520; A user may pull a top article 520A from opening 516A or a top article 520B from opening 5168. Note that conveniently dispensers with multiple openings may allow dispensing variously sized articles, by choosing and opening and pulling out a top article out through the selected opening (not shown).

It is notable that the structure of the top article in a new stack (from which no articles have been drawn as yet) may be different from the structure of the articles below in the stack, since the handle is not raiseable by the action of pulling out an article above it, The bottom article in a stack may not include a handle below it, as there are no articles left to draw out when the bottom article is drawn out. Therefore, it has been most convenient to define the articles above as each having a handle above a sticky cover, even though most articles in a stack also have a handle coupled below the same cover.

Comparing to for example plasters, which are covers with skin-adhesive material wrapped in wrapping, the handles in some of the embodiments above may act as both means to pull their coupled articles for application, as well as being a non-stick layer that protects the skin-adherent material of a cover before pulling out the cover. This way, there is minimal wasted material, and the cover is pulled out fully exposed, while the wrapping remains behind to act as the handle of the next article.

It is stressed that all of the embodiments described above and in the figures are considered to be suitable for use for a multitude of skin-sticky covers, including but not limited to:

Adhesive bandages of all shapes and sizes; nicotine patches; anti snoring patches for opening nostrils; medicinal patches for drugs that can be absorbed by the skin; electronic patches that are used for electromagnetic monitoring (for monitoring the heart, brain and so on); Electronic patches that contain RFID components; hormone patches (Including pregnancy preventing patches; and skin care patches, for cleaning pores and/or preventing acne. It is further stressed that the invention includes methods and apparatuses for applying sticky articles of all kinds, such as stamps and bumper stickers, which include providing a cover with a side adhesive to a particular surface, and an opposite side to which a protective element and handle are stuck, the articles being connected to each other in one the configurations in the embodiments described above, Such methods and apparatuses have the same advantageous features: ease of peeling off a cover, and minimal waste of material.

It should be clear that the description of the embodiments and attached Figures set forth in this specification serves only for a better understanding of the invention, without limiting its scope as covered by the following Claims.

It should also be clear that a person skilled in the art, after reading the present specification can make adjustments or amendments to the attached Figures and above described embodiments that would still be covered by the following Claims.

The invention claimed is:

1. A sticky article comprising:
a skin-adherent cover having a first side provided with skin adhesive material, a second opposite side, and edges;
a first handle and a second handle; and
a first protective element and a second protective element protective of the cover, wherein each protective element extends to or beyond said edges of the cover, wherein the first protective element adheres to said second opposite side less than said first side comprising skin-adhesive material adheres to skin, and the second protective element attached to said first side comprises skin-adhesive material, and wherein
said first handle is coupled to the first protective element and said second handle is coupled to the second protective element,
and the article is adapted and configured to:
allow detachment of said second element and said second handle from said skin adhering cover when said first handle and said second handles are pulled apart while the first element remains attached to the cover, and to
allow detaching the first element from an adhered cover by twisting the first handle.

2. The article of claim 1, further comprising at least one liner non-adherently contacting the skin-adhesive material, and wherein the second protective element adheres to the first protecting element.

3. A stack of articles of claim 1, wherein the second handle of each article above a bottom article in the stack is a first handle of an adjacent article below.

4. A dispenser comprising at least one stack of articles of claim 3 and a cartridge comprising walls, at least one bottom and at least one opening.

5. The article of claim 1, wherein the cover is selected from one or more of the group: skin patch, poultice, plaster and bandage.

* * * * *